USO11452492B2

(12) United States Patent
Junio

(10) Patent No.: US 11,452,492 B2
(45) Date of Patent: Sep. 27, 2022

(54) SYSTEM AND METHOD FOR POSITIONING AN IMAGING DEVICE

(71) Applicant: MAZOR ROBOTICS LTD., Caesarea (IL)

(72) Inventor: Dany Junio, Tel Aviv-Jaffa (IL)

(73) Assignee: Mazor Robotics Ltd., Caesarea (IL)

( * ) Notice: Subject to any disclaimer, the term of this patent is extended or adjusted under 35 U.S.C. 154(b) by 249 days.

(21) Appl. No.: 16/854,011

(22) Filed: Apr. 21, 2020

(65) Prior Publication Data
US 2021/0321971 A1 Oct. 21, 2021

(51) Int. Cl.
*A61B 6/00* (2006.01)
*A61B 6/04* (2006.01)
*G06T 7/00* (2017.01)

(52) U.S. Cl.
CPC ............ *A61B 6/547* (2013.01); *A61B 6/0492* (2013.01); *A61B 6/4435* (2013.01); *A61B 6/505* (2013.01); *A61B 6/5211* (2013.01); *G06T 7/0012* (2013.01); *G06T 2207/30012* (2013.01)

(58) Field of Classification Search
None
See application file for complete search history.

(56) References Cited

U.S. PATENT DOCUMENTS

| 7,142,633 | B2 | 11/2006 | Eberhard et al. |
| 7,231,073 | B2 | 6/2007 | Tamaka |
| 7,366,562 | B2 | 4/2008 | Dukesherer et al. |
| 8,103,079 | B2 | 1/2012 | Saito |
| 9,463,073 | B2 | 10/2016 | Gill et al. |
| 9,491,415 | B2 | 11/2016 | Deurz et al. |
| 9,968,502 | B2 | 5/2018 | Hight et al. |
| 10,058,338 | B2 | 8/2018 | Shoham |
| 10,426,554 | B2 | 10/2019 | Siewerdsen et al. |
| 10,478,143 | B2 | 11/2019 | Merlet et al. |
| 10,551,821 | B2 | 2/2020 | Yamaguchi et al. |
| 2009/0278702 | A1* | 11/2009 | Graumann ............ A61B 34/20 340/686.2 |
| 2015/0335390 | A1 | 11/2015 | Gill |
| 2016/0253797 | A1 | 9/2016 | Lang et al. |
| 2018/0021102 | A1 | 1/2018 | Azizian et al. |
| 2018/0318012 | A1 | 11/2018 | Amo et al. |

(Continued)

FOREIGN PATENT DOCUMENTS

| CN | 110599508 | 12/2019 |
| DE | 102008050572 | 4/2010 |
| EP | 3578128 | 12/2019 |

(Continued)

OTHER PUBLICATIONS

U.S. Appl. No. 16/853,990, filed Apr. 21, 2020, Junio.

(Continued)

*Primary Examiner* — Hoon K Song
(74) *Attorney, Agent, or Firm* — Sheridan Ross P.C.

(57) ABSTRACT

A method of positioning an imaging device relative to a patient, comprising positioning a reference marker adjacent a desired field of scan corresponding to an anatomical element of a patient; and causing an imaging device to align with the reference marker, based on tracking information received from a navigation system, the tracking information corresponding to the reference marker and a navigated tracker disposed on the imaging device.

20 Claims, 4 Drawing Sheets

(56) References Cited

U.S. PATENT DOCUMENTS

2020/0214656 A1* 7/2020 Shirota ................ A61B 6/4452
2021/0228281 A1* 7/2021 Calloway .............. G06T 19/006

FOREIGN PATENT DOCUMENTS

| WO | WO 2010/064234 | 6/2010 |
| WO | WO 2019/012520 | 1/2019 |
| WO | WO 2019/169178 | 9/2019 |

OTHER PUBLICATIONS

Han et al. "A targeting method for robot-assisted percutaneous needle placement under fluoroscopy guidance," Computer Assisted Surgery, 2019, vol. 24, No. S1, pp. 44-52.

International Search Report and Written Opinion for International (PCT) Patent Application No. PCT/US2021/026429, dated Jul. 26, 2021, 8 pages.

U.S. Appl. No. 16/853,990, filed Apr. 21, 2020.

* cited by examiner

SYSTEM AND METHOD FOR POSITIONING AN IMAGING DEVICE

FIELD

The present technology is related generally to imaging devices and, more particularly, to positioning and aligning an imaging device for robotic surgery.

BACKGROUND

Navigation systems are used during surgical operations or procedures to provide direct or indirect guidance to a surgical team. The navigation system can include a camera and/or other sensor(s) for tracking one or more reference markers, which in turn may be attached to one or more anatomical elements of the patient, one or more surgical instruments, one or more imaging devices, and/or one or more other objects in the operating room.

Before a navigation system may be used in connection with a surgical procedure, a coordinate system of the navigation system must be correlated to a coordinate system of the patient, in a process referred to as registration. In robotically assisted surgical procedures, the coordinate system of a surgical robot must also be correlated with the coordinate system of the patient and/or of the navigation system. Proper registration prior to starting a surgical procedure is crucial to ensure that a preoperative surgical plan can be accurately carried out during surgery.

The registration process typically involves taking one or more intraoperative images, which is/are then compared to and aligned with one or more pre-operative images so that a location in one image corresponds to the same location in the other image. However, for an intraoperative image to be useful for registration, the image must include the subject anatomy or anatomical element. This is straightforward when the subject anatomy or anatomical element is readily visible (e.g., a foot, an arm), but less so for internal anatomy (e.g., a spine or element thereof). In the latter instance, multiple images may be taken before an image that properly shows the desired anatomy or anatomical element is captured.

SUMMARY

Particularly for imaging devices that use X-rays or other forms of potentially harmful radiation, the taking of unnecessary images of a patient is undesirable, both for the patient and for others in the operating room that may be exposed to the radiation. Moreover, taking multiple unnecessary images wastes valuable operating room time, thus increasing costs. Systems, devices, and methods are needed that shorten the amount of time needed to complete the registration process.

Embodiments of the present disclosure advantageously provide objective approaches to positioning an imaging device and a robot for robotic surgery. Embodiments of the present disclosure beneficially decrease overall operating time (and cost) by reducing the initial setup time needed for registration. Embodiments of the present disclosure may also beneficially reduce radiation exposure to the patient by reducing the number of images needed to align the imaging device.

A method for positioning an imaging device relative to a patient according to one embodiment of the present disclosure may comprise aligning a reference marker with an anatomical feature of a patient; and causing an imaging device to align with the reference marker, based on tracking information received from a navigation system, the tracking information corresponding to the reference marker and a navigated tracker disposed on the imaging device.

The method may further comprise: receiving image data from the imaging device; processing the image data using an image processing algorithm to automatically determine whether an entirety of the anatomical feature is in the image data, to yield an anatomical determination; generating a repositioning requirement based on the anatomical determination; and transmitting instructions based on the repositioning requirement and configured to cause the imaging device to move if the entirety of the anatomical feature is not in the image data.

The reference marker may identify a first axis and a second axis orthogonal to the first axis. Causing the imaging device to align with the reference marker may comprise causing the imaging device to move into alignment with the first axis and the second axis. Causing the imaging device to move into alignment with the first axis and the second axis may comprise causing the imaging device to be moved to a position offset from at least one of the first axis or the second axis by a predetermined amount. Causing the imaging device to move into alignment with the first axis and the second axis may comprise causing the imaging device to move in a direction orthogonal to the first axis and the second axis. The method may further comprise: receiving second image data from the imaging device; and causing the imaging device to move again if the entirety of the anatomical feature is not in the second image data. The imaging device may comprise an O-arm. The anatomical feature may comprise one or more vertebrae. The reference marker may comprise one or more navigation spheres. The reference marker may be positioned automatically by a robot.

Another method for positioning an imaging device relative to a patient according to one embodiment of the present disclosure comprises: positioning a reference marker adjacent a desired field of scan corresponding to an anatomical element of a patient; and causing an imaging device to align with the reference marker, based on tracking information received from a navigation system, the tracking information corresponding to the reference marker and a navigated tracker disposed on the imaging device.

The method may further comprise receiving image data from the imaging device; processing the image data using an image data processing algorithm to automatically determine whether an entirety of the anatomical element is in the image data; transmitting instructions configured to cause the imaging device to move again if the entirety of the anatomical feature is not in the image data; and transmitting instructions configured to cause the imaging device to perform at least one full scan of the anatomical element when the entirety of the anatomical element is in the image data.

The reference marker may identify a first axis and a second axis orthogonal to the first axis. Causing the imaging device to align with the reference marker may comprise causing the imaging device to move into alignment with the first axis and the second axis. Causing the imaging device to move into alignment with the first axis and the second axis may comprise causing the imaging device to move to a position offset from at least one of the first axis or the second axis by a predetermined amount. Causing the imaging device to move may comprise causing the imaging device to move in a direction orthogonal to the first axis and the second axis. The imaging device may comprise an O-arm. The reference marker may comprise one or more navigation spheres. The reference marker may be positioned automatically by a robot.

A system for positioning an imaging device relative to a patient according to one embodiment of the present disclosure comprises: at least one communication interface for communicating with an imaging device and a navigation system; a processor; and a memory storing instructions for execution by the processor. The instructions, when executed, cause the processor to: cause a reference marker to be positioned adjacent a desired field of scan corresponding to an anatomical element of a patient; and cause an imaging device to align with the reference marker, based on tracking information received from a navigation system, the tracking information corresponding to the reference marker and a navigated tracker disposed on the imaging device.

The instructions, when executed, may further cause the processor to: receive, via the communication interface, image data from the imaging device; process the image data using an image data processing algorithm to automatically determine whether an entirety of the anatomical element is in the image data to yield an anatomical determination; generate a repositioning requirement based on the anatomical determination; and transmit instructions based on the repositioning requirement and configured to cause the imaging device to move if the entirety of the anatomical element is not in the image data.

Causing the reference marker to be positioned adjacent a desired field of scan may comprise causing a robot to position the reference marker adjacent a desired field of scan such that the reference marker is aligned with the anatomical element. The imaging device may comprise an O-arm. The anatomical feature may comprise one or more vertebrae.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
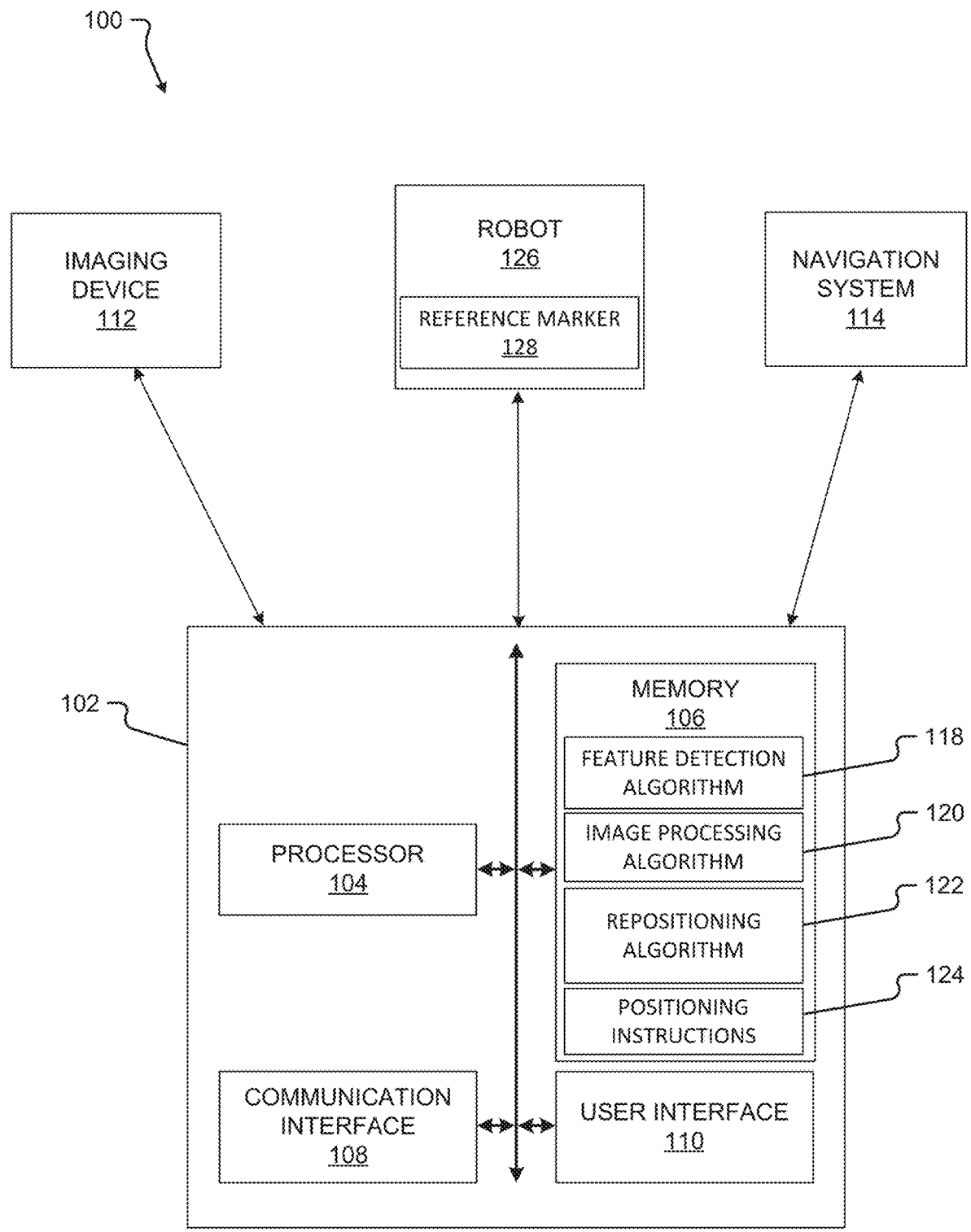
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors;

AMD Athlon processors; AMD Phenom processors; Apple A10 or 10× Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Turning first to FIG. 1, a block diagram of a system 100 according to at least one embodiment of the present disclosure is shown. The system 100 may be used to process image data; execute a feature detection algorithm, an image processing algorithm, and/or a repositioning algorithm; make a position and/or location determination; and/or carry out other aspects of one or more of the methods disclosed herein. The system 100 comprises a computing device 102, an imaging device 112, a navigation system 114, and/or a robot 126.

The computing device 102 comprises a processor 104, a memory 106, a communication interface 108, and a user interface 110. Systems such as the system 100 according to other embodiments of the present disclosure may comprise more or fewer components than the system 100.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, and/or the navigation system 114.

The memory 106 may be or comprise RAM, DRAM, SDRAM, other solid-state memory, any memory described herein, or any other non-transitory memory for storing computer-readable data and/or instructions. The memory 106 may store information or data useful for completing any step of the method 200 described herein. The memory 106 may store, for example, one or more feature detection algorithms 118, one or more image processing algorithms 120, one or more repositioning algorithms 122, and/or one or more positioning instructions 122. Such instructions or algorithms may, in some embodiments, be organized into one or more applications, modules, packages, layers, or engines. The algorithms and/or instructions may cause the processor 104 to manipulate data stored in the memory 106 and/or received from the imaging device 112 and/or from the navigation system 114.

The computing device 102 may also comprise a communication interface 108. The communication interface 108 may be used for receiving image data or other information from an external source (such as the imaging device 112, the robot 126, and/or the navigation system 114), and/or for transmitting instructions, images, or other information to an external system or device (e.g., the navigation system 114, another computing device 102, and/or the robot 126). The communication interface 108 may comprise one or more wired interfaces (e.g., a USB port, an ethernet port, a Firewire port) and/or one or more wireless interfaces (configured, for example, to transmit information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, and/or any other device for receiving information from a user and/or for providing information to a user. The user interface 110 may be used, for example, to receive a user selection or other user input regarding positioning a reference marker 128 adjacent a desire field of scan corresponding to an anatomical feature of a patient; to receive user input regarding causing the imaging device to align with the reference marker 128; to receive user input regarding processing received image data to determine whether an entirety of the anatomical feature is in the image data; to receive a user selection or other user input regarding transmitting instructions configured to cause the imaging device 112 to move if the entirety of the anatomical feature is not in the image data; to display the image data received from the imaging device 112; and/or to display the instructions for moving the imaging device 112 or causing the imaging device 112 to move. In some embodiments, the user interface 110 may be useful to allow a surgeon or other user to modify the first instructions, the second instructions, or other information displayed.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 is operable to image an anatomical element or feature of a patient (e.g., a spine region or one or more vertebrae) to yield image data (e.g., image data depicting or corresponding to a spinal column of a patient). "Image data" as used herein refers to the data generated or captured by an imaging device, including in a machine-readable form, a graphical form, and in any other form. In various examples, the image data may comprise data corresponding to a complete anatomical feature of a patient, or to a portion thereof (e.g., the entire spinal column of the patient or to a portion thereof). The imaging device 112 may be an O-arm, a C-arm, a G-arm, or any other device x-ray based imaging device (e.g., a fluoroscope, a CT scanner, or other X-ray machine), but may alternatively be a magnetic resonance imaging (MRI) scanner, an ultrasound scanner, an optical computed tomography scanner, or any other imaging device suitable for obtaining images of an anatomical element of a patient. The imaging device 112 may be configured with a source positioned underneath a patient, and a detector positioned above the patient—in which event the X-rays or other electromagnetic signals or waves pass through the patient and then through any reference marker 128 positioned above the patient before reaching the detector. The imaging device 112 may be capable of selectively taking a 2D image (obtained, for example, without moving the source or detector or other imaging equipment within the imaging device 112) or a 3D image (obtained, for example, by rotating the source and detector or other imaging equipment in a semi-circle or complete circle around the patient).

The navigation system 114 may provide navigation for a surgeon and/or a surgical robot during an operation. The navigation system 114 may be any known or future navigation system, including, for example, the Medtronic StealthStation™ S8 surgical navigation system. In various embodiments, the navigation system 114 may be used to track a position of the imaging device 112 (or, more particularly, of a navigated tracker attached to the imaging device 112), and of the reference marker 128 (which may be attached to the robot 126 or may be separate from the robot 126). The navigation system 114 may include a camera or other sensor(s) for tracking one or more reference markers, navigated trackers, or other objects within the operating room. The navigation system 114 may include a display for displaying one or more images from an external source (e.g., the computing device 102, imaging device 112, or other source) or a video stream from the camera or other sensor of the navigation system 114. The navigation system 114 may be, for example, the same as or similar to a navigation system described by U.S. Pat. No. 7,366,562, entitled "Method and Apparatus for Surgical Navigation, filed Oct. 17, 2003, and assigned to Medtronic Navigation Inc., the entirety of which is hereby incorporated by reference herein.

The robot 126 may be any surgical robot or surgical robotic system. The robot 126 may be or comprise, for example, the Mazor X™ Stealth Edition robotic guidance system. The robot 126 may comprise a robotic arm, and the robotic arm may hold or otherwise support a reference marker 128. The reference marker 128 may be disposed on an end of the robotic arm in some examples, while in other examples the reference marker 128 may be disposed on any portion of the robotic arm or of the robot 126. The reference marker 128 may define a first axis and a second axis orthogonal to the first axis. The reference marker 128 may be or comprise a marker having any visible geometry useful for the purposes described herein. In some embodiments, the reference marker 128 may be a navigated reference marker, while in other embodiments, the reference marker 128 may not be navigated marker.

Figure 2:
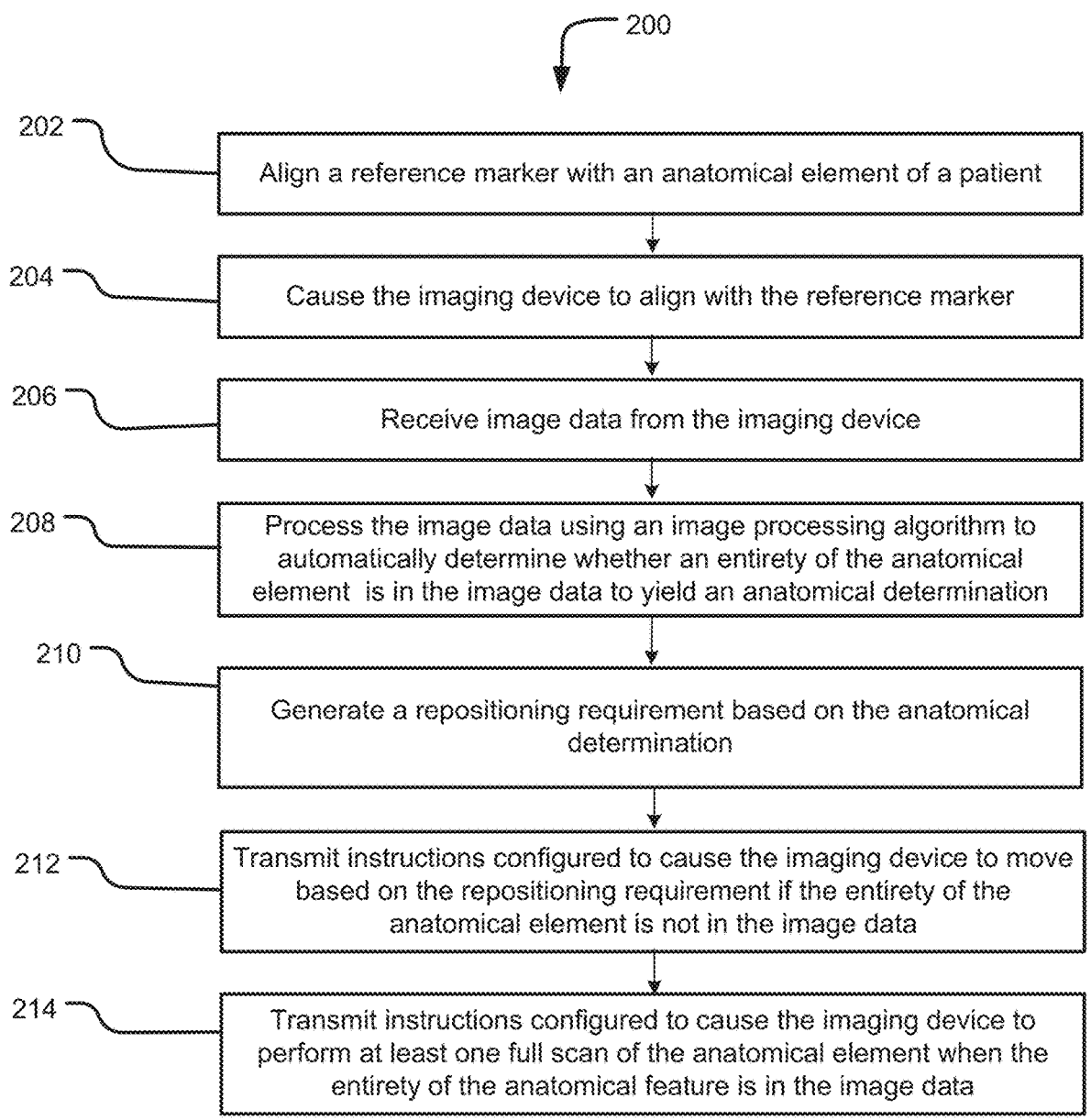
FIG. 2 is a flowchart of a method according to at least one embodiment of the present disclosure.

Turning now to FIG. 2, a method 200 for positioning an imaging device 112 relative to a patient in connection with a surgical procedure according to embodiments of the present disclosure may be executed in whole or in part on a computing device 102. The positioning and alignment are performed during initial setup of a surgical operation, and may be or comprise part of a registration process. The surgery may be performed by a surgical robot, a surgeon, or a combination of both.

The method 200 comprises aligning a reference marker with an anatomical element of a patient (step 202). As illustrated in FIG. 3A, for example, the reference marker 128 may be positioned directly on the patient 302. The reference marker 128 may be positioned anywhere on or near the patient 302 including, but not limited to, the head, back, legs, or arm of the patient 302. In other examples, the reference marker 128 may be held over the patient 302 by a robotic arm of the robot 126. Whether resting on, held on, or held above the patient 302, the reference marker 128 is aligned with the anatomical element of the patient 302. For example, if the anatomical element to be imaged is a spine of a patient (or a portion thereof), then the reference marker 128 may be positioned directly over the spine and aligned with an axis of the spine (or of the relevant portion thereof), so that a first axis of the reference marker 128 is aligned with an axis of the spine and a second, orthogonal axis of the reference marker 128 is orthogonal to an axis of the spine. If the spine is healthy, then the first axis of the reference marker 128 may be aligned with a head-to-foot axis of the patient 302, and a second axis of the reference marker 128 may be aligned with a left-to-right or lateral axis of the patient 302. However, if the spine is unhealthy (e.g., if the spine exhibits scoliosis), then the reference marker 128, when aligned with the spine, may not be aligned with a head-to-foot axis and/or a left-to-right or lateral axis of the patient 302. Regardless, the first axis and the second axis may each be positioned in a horizontal or substantially horizontal plane.

The reference marker 128 may be or comprise one or more navigation markers or spheres and may be configured for detection and tracking by an optical (visual wavelength) navigation system, an infrared navigation system, an electromagnetic navigation system, or any other navigation system. Aligning the reference marker 128 with the anatomical element of the patient 302 may comprise transmitting instructions to the robot 126 via the communication interface 108 to cause the robot 126 to automatically position the reference marker 128, and/or to position the reference marker 128 based on guidance provided via the user interface 110.

Figure 3:
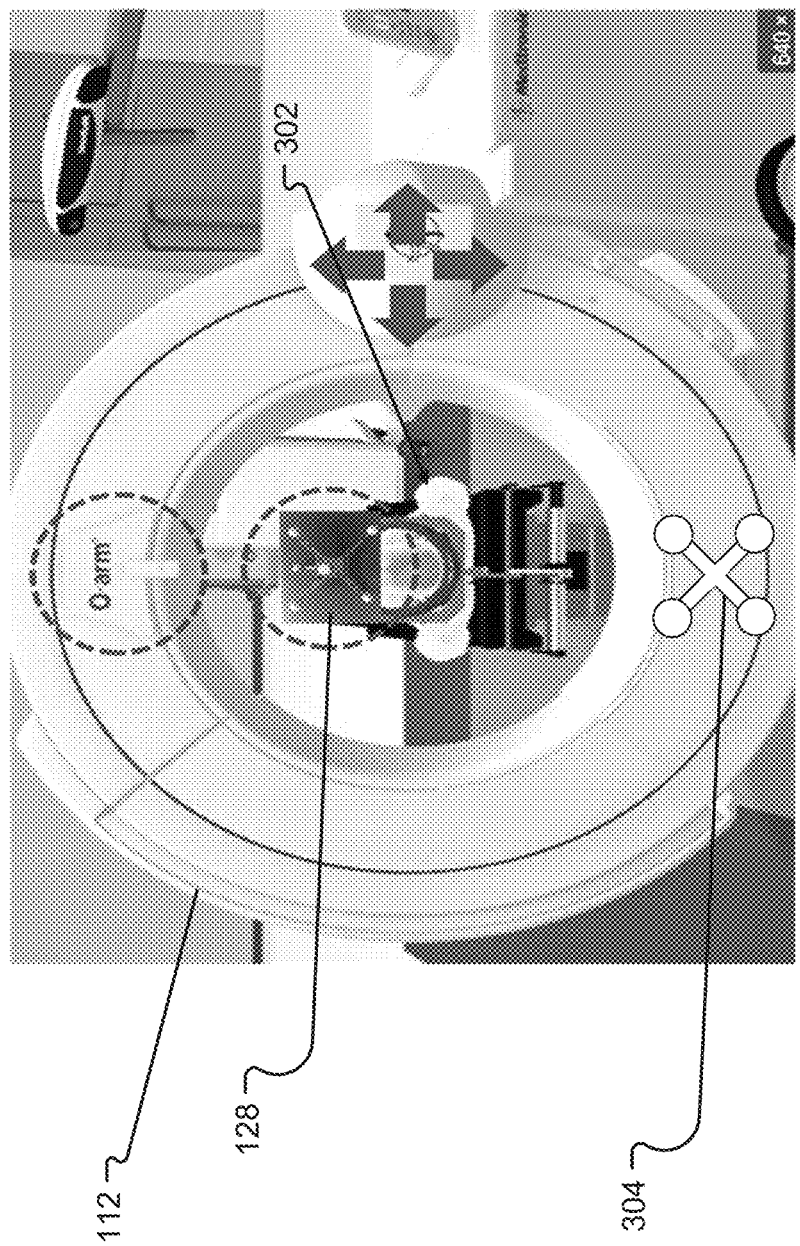
FIG. 3 illustrates an imaging device and a reference frame disposed on a patient anatomy according to at least one embodiment of the present disclosure.

The method 200 also comprises causing an imaging device 112 to align with the reference marker 128, based on tracking information received from a navigation system 114, the tracking information corresponding to the reference marker 128 and a navigated tracker 304 disposed on the imaging device 112 (step 204). As shown in FIG. 3, the navigated tracker 304 is disposed on an O-arm imaging device 112, though in other examples, the imaging device 112 may be a C-arm, a G-arm, a CT scanner, a fluoroscopy device, an MRI scanner, or another imaging device.

The tracking information may be based on a marker tracking algorithm 118 executed by the processor 104. The algorithm 118 may receive one or more images or streaming video from an optical camera, an infrared camera, or any other type of camera as input. In some embodiments, the algorithm 118 may initially detect and track the reference marker 128 and/or the navigated tracker 304 by comparing the image or video data to preoperative image data with or without a reference marker 128 and/or a navigated tracker 304. In other embodiments, the algorithm 118 may identify one or more shapes corresponding to the reference marker 128 in the image or video data based on input to the algorithm 118 regarding the shape. For example, the algorithm 118 may receive input (e.g., from a user via the user interface 110) that the reference marker 128 reference marker 128 and/or the navigated tracker 304 is a square and may search for a square or substantially square shape in the image or video data. In other embodiments, the shape may include, but is not limited to, a circle, an oval, a star, a pentagon, or the like. The algorithm 118 may also calculate a relative spatial location of the reference marker 128 and the navigated tracker 304 to determine a position of the imaging device 112 based on a position of the reference marker 128.

The imaging device 112 may, in some embodiments, be aligned to capture both the reference marker 128 and the anatomical element. In some embodiments, the imaging device 112 may align with both the first axis and the second axis of the reference marker 128. Once aligned with the first axis and the second axis of the reference marker 128, the imaging device 112 need only align with a third axis orthogonal to first axis and the second axis to ensure proper imaging of the anatomical element in question. For example, the direction orthogonal to the first axis and the second axis would extend in the anterior-posterior direction (e.g., in a vertical plane). Thus, once aligned with the first and second axis of the reference marker 128, the imaging device 112 need only be adjusted in the anterior-posterior direction, or along a depth of the patient 302.

In various embodiments, aligning the imaging device 112 with the reference marker 128 comprises positioning the imaging device 112 so that one axis of the imaging device 112 is coaxial with the first axis of the reference marker 128, and another axis of the imaging device 112 is coaxial with the second axis of the reference marker 128. In other embodiments, aligning the imaging device 112 with the reference marker 128 comprises positioning the imaging device 112 so that one axis of the imaging device 112 is parallel to but offset from the first axis or the second axis of the reference marker 128. Another axis of the imaging device 112 may be parallel to but offset from, or coaxial with, the second axis or the first axis, respectively, of the reference marker 128.

The imaging device 112 may include one or more motors and/or one or more controllers configured to automatically move the imaging device 112 into position. Further, though the imaging device 112 may be capable of automatically moving into position, a surgeon or other user may control when the imaging device 112 moves. For example, the imaging device 112 may be configured such that the surgeon or other user must actively press a safety button to enable the imaging device 112 to move, and release of the safety button may cause the imaging device 112 to stop moving even if the imaging device 112 has not yet reached a target position.

The method 200 further comprises receiving image data from the imaging device 112 (step 206). The image data may correspond to a single 2D image taken by the imaging device 112 once it has been aligned with the reference marker 128. The image data is generated by the imaging device 112, but may be received directly from the imaging device 112 or indirectly via any other source. The image data may be received via the communication interface 108. Processing of the image data may include applying the image processing algorithm 120 to the image data (or, alternatively, inputting the image data to the image processing algorithm 120), which algorithm 120 may apply one or more filters to the image data to prepare the image data for further processing. The image data may include or correspond to, for example, the image data 400 shown in FIGS. 4A and 4B.

Figures 4A, 4B:
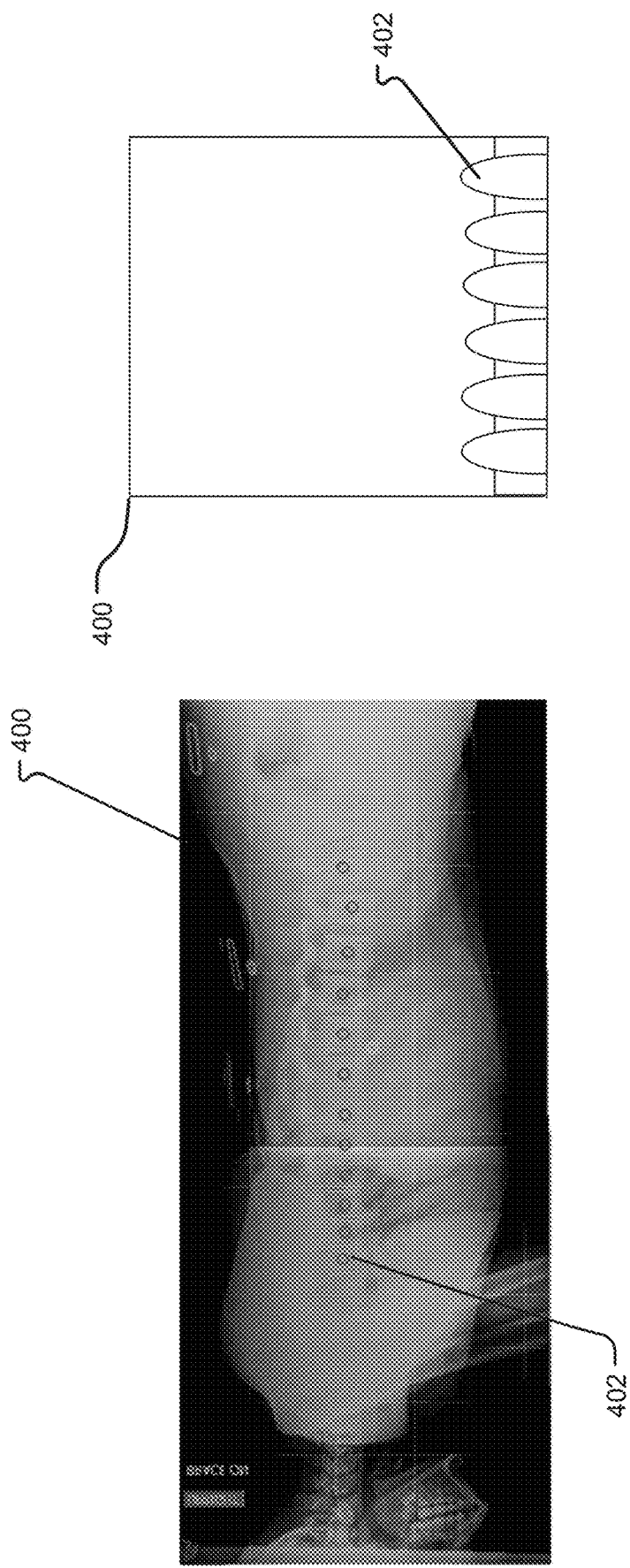
FIG. 4A is a lateral image of a spine region according to at least one embodiment of the present disclosure.
FIG. 4B is another lateral image of a spine region according to at least one embodiment of the present disclosure.

The method 200 further comprises processing the image data 400 using a feature detection algorithm 118 to automatically identify one or more anatomical features in the image data 400 and determine whether an entirety of the anatomical element in question is in the image data, thus yielding an anatomical determination (step 208). The anatomical element 402, as shown in FIGS. 4A and 4B, may be identified by executing the feature detection algorithm 118 with the processor 104. The feature detection algorithm 118 may, in some embodiments, use a neural network, machine learning, artificial intelligence, or the like, to process the image data 400. The feature detection algorithm 118 may be configured to segment one or more anatomical features identified in the image data 400 and evaluate the resulting segments, as illustrated in FIG. 4A (in which the endplates and center points of the spinal vertebrae have been identified). In some embodiments, the feature detection algorithm 118 may identify one or more objects in the image data 400 and compare them to one or more known shapes to determine whether the identified objects correlate to a known shape and can therefore be identified as a known anatomical element 402. In other embodiments, the feature detection algorithm 118 may be generated by a machine learning engine based on training data. The training data may be or comprise, for example, a plurality of images of anatomical elements that have been marked so that the machine learning engine can identify correlations between different images of the same anatomical element and thus learn to identify the anatomical element in question.

In other embodiments, a surgeon or other user may identify the anatomical element 402 by providing one or more inputs via a user interface 110. In such embodiments, the identification of the anatomical element 402 may be based on the image data 400 and/or additional information obtained from the user.

Whether an entirety of the anatomical element 402 (e.g., a spine region) is represented in the image data 400 may be determined automatically by executing the feature detection algorithm 118 with the processor 104 to yield the anatomical determination. The anatomical determination corresponds to whether the imaging device 112 is misaligned. More specifically, if only a portion or none of the anatomical element 402 is represented in the image data 400, then the imaging device 112 needs to be moved before completing a full registration scan. Conversely, if all of the anatomical element 402 is in the image data 400, as shown in FIG. 4A, then the imaging device 112 is properly aligned and can proceed with a full registration scan.

The method 200 also comprises generating a repositioning requirement based on the anatomical determination (step 210). The repositioning requirement may be calculated using the repositioning algorithm 122. The algorithm 122 determines if the imaging device 112 requires repositioning based on whether the imaging device 112 is misaligned and, if so, calculates the new position for the imaging device 112. The algorithm 122 may comprise one or more principles of geometry, trigonometry, and/or other mathematical subjects to determine how to move the imaging device 112 to capture more or all of the anatomical element 402 in a subsequent image.

The repositioning requirement may be based on the anatomical element 402 that is partially or fully not represented in the image data 400. For example, a portion of the anatomical element 402 (e.g., a spine region) in FIG. 4B is not represented in the image data 400. Based on a portion of the anatomical element 402 that is represented in the image data 400, a direction or predicted position of the portion of the anatomical element 402 not represented in the image 400 can be generated based on the known portion of the anatomical element 402 that is represented in the image data 400. For example, in FIG. 4B, the portion of the anatomical element 402 not represented in the image data 400 is to a bottom side of a frame of the image data 400 and thus, the predicted position of the portion not represented in the image data 400 would be to the bottom of the frame. The algorithm 122 can calculate a needed change in position or new position for the imaging device 112 to capture all or at least a greater portion of the anatomical element 402 in a subsequent image.

If none of the anatomical element 402 is represented in the image data 400, then the repositioning requirement may be calculated to cause the imaging device 112 to move in increments in either direction along an axis orthogonal to the first axis and the second axis of the reference marker (e.g., towards an anterior and/or towards a posterior of the patient) until the anatomical element 402 is identified. In other examples, the surgeon or other user may move the imaging device 112 manually until the anatomical element 402 is identified.

The method 200 further comprises transmitting positioning instructions 124 comprising instructions configured to cause the imaging device 112 to move based on the repositioning requirement if the entirety of the anatomical element 402 is not in the image (step 212). In various embodiments, the instructions are configured to reposition the imaging device 112 based on a portion of the anatomical element 402 not represented in the image data 400, as described above with respect to step 212. In further embodiments, the second instructions are configured to iteratively and/or incrementally reposition the imaging device 112 until an anatomical element 402 is identified.

In various examples, the instructions may be machine readable to cause the imaging device 112 to automatically move. In other examples, the second instructions may be manual instructions displayed on the user interface 110 instructing the user to move the imaging device 112.

The method 200 further comprises transmitting instructions configured to cause the imaging device 112 to perform at least one full scan of the anatomical element 402 when the entirety of the anatomical feature 402 is in the image data 400 (step 216). In some embodiments, the imaging device 112 is an O-arm and performing at least one full scan comprises performing a 3-D scan.

If the first image data 400 does not include all of the anatomical element 402, the method 200 may further comprise (before step 214) receiving second image data from the imaging device 112 (e.g., in the same manner as or in a similar manner to step 206), processing the second image data (e.g., in the same manner as or in a similar manner to step 208), generating a repositioning requirement (e.g., in the same manner as or in a similar manner to step 210), and transmitting second instructions configured to cause the imaging device 112 to move again in a direction orthogonal to the first axis and the second axis of the reference marker 128 (e.g., in the same manner as or in a similar manner to step 212). In other words, steps 206 to 212 may be repeated until the entirety of the anatomical element 402 is in the image data or subsequent image data.

The methods and systems described provide an efficient method for positioning and aligning an imaging device for robotic surgery. Further, the methods and systems reduce the amount of imaging needed for each iteration (e.g., a single lateral scan opposed to a full 3-D scan), thereby reducing the amount of to which a patient is exposed. The method is simple to implement and portions of or the entire method may be automated, thereby reducing initial setup time and overall operation time.

As may be appreciated based on the foregoing disclosure, the present disclosure encompasses methods with fewer than all of the steps identified in FIG. 2 (and the corresponding description), as well as methods that include additional steps beyond those identified in FIG. 2 (and the corresponding description).

One or more aspects of the present disclosure may be the same as or similar to one or more corresponding aspects described in a U.S. patent application Ser. No. 16/853,990, filed contemporaneously herewith by the same applicant, entitled "System and Method for Aligning an Imaging Device" and naming the same inventor as the present application, which is hereby incorporated herein by reference in its entirety.

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method of positioning an imaging device relative to a patient, comprising:
   positioning a reference marker adjacent a desired field of scan corresponding to an anatomical element of a patient;
   causing an imaging device to align with the reference marker, based on tracking information received from a navigation system, the tracking information corresponding to the reference marker and a navigated tracker disposed on the imaging device;
   receiving image data from the imaging device;
   processing the image data using an image data processing algorithm to automatically determine whether an entirety of the anatomical element is in the image data to yield an anatomical determination;
   generating a repositioning requirement based on the anatomical determination; and
   transmitting instructions based on the repositioning requirement and configured to cause the imaging device to move if the entirety of the anatomical element is not in the image data.

2. The method of claim 1, wherein the image data is in at least one of a machine-readable form and a graphical form.

3. The method of claim 1, wherein the reference marker identifies a first axis and a second axis orthogonal to the first axis, and further wherein causing the imaging device to align with the reference marker comprises causing the imaging device to move into alignment with the first axis and the second axis.

4. The method of claim 3, wherein causing the imaging device to move into alignment with the first axis and the second axis comprises causing the imaging device to be moved to a position offset from at least one of the first axis or the second axis by a predetermined amount.

5. The method of claim 3, wherein causing the imaging device to move comprises causing the imaging device to move in a direction orthogonal to the first axis and the second axis.

6. The method of claim 2, further comprising:
receiving second image data from the imaging device; and
causing the imaging device to move again if the entirety of the anatomical element is not in the second image data.

7. The method of claim 1, wherein the imaging device comprises an O-arm.

8. The method of claim 1, wherein the anatomical element comprises one or more vertebrae.

9. The method of claim 1, wherein the reference marker is positioned automatically by a robot.

10. A method of positioning an imaging device relative to a patient, comprising:
positioning a reference marker adjacent a desired field of scan corresponding to an anatomical element of a patient;
causing an imaging device to align with the reference marker, based on tracking information received from a navigation system, the tracking information corresponding to the reference marker and a navigated tracker disposed on the imaging device;
receiving image data from the imaging device;
processing the image data using an image data processing algorithm to automatically determine whether an entirety of the anatomical element is in the image data;
transmitting instructions configured to cause the imaging device to move again if the entirety of the anatomical element is not in the second image data; and
transmitting instructions configured to cause the imaging device to perform at least one full scan of the anatomical element when the entirety of the anatomical element is in the image data.

11. The method of claim 10, wherein the image data is in at least one of a machine-readable form and a graphical form.

12. The method of claim 10, wherein the reference marker identifies a first axis and a second axis orthogonal to the first axis, and further wherein causing the imaging device to align with the reference marker comprises causing the imaging device to move into alignment with the first axis and the second axis.

13. The method of claim 12, wherein causing the imaging device to move into alignment with the first axis and the second axis comprises causing the imaging device to move to a position offset from at least one of the first axis or the second axis by a predetermined amount.

14. The method of claim 12, wherein causing the imaging device to move comprises causing the imaging device to move in a direction orthogonal to the first axis and the second axis.

15. The method of claim 10, wherein the imaging device comprises an O-arm.

16. The method of claim 10, wherein the reference marker is positioned automatically by a robot.

17. A system for positioning an imaging device relative to a patient comprising:
at least one communication interface for communicating with an imaging device and a navigation system;
a processor; and
a memory storing instructions for execution by the processor that, when executed, cause the processor to:
cause a reference marker to be positioned adjacent a desired field of scan corresponding to an anatomical element of a patient,
cause an imaging device to align with the reference marker, based on tracking information received from a navigation system, the tracking information corresponding to the reference marker and a navigated tracker disposed on the imaging device,
receive, via the communication interface, image data from the imaging device,
process the image data using an image data processing algorithm to automatically determine whether an entirety of the anatomical element is in the image data to yield and anatomical determination,
generate a repositioning requirement based on the anatomical determination, and
transmit instructions based on the repositioning requirement and configured to cause the imaging device to move if the entirety of the anatomical element is not in the image data.

18. The system of claim 17, wherein the image data is in at least one of a machine-readable form and a graphical form.

19. The system of claim 17, wherein causing the reference marker to be positioned adjacent a desired field of scan comprises causing a robot to position the reference marker adjacent a desired field of scan such that the reference marker is aligned with the anatomical element.

20. The system of claim 17, wherein the anatomical element comprises one or more vertebrae.

* * * * *